United States Patent [19]
McVenes et al.

[11] Patent Number: 5,489,294
[45] Date of Patent: Feb. 6, 1996

[54] STEROID ELUTING STITCH-IN CHRONIC CARDIAC LEAD

[75] Inventors: Rick D. McVenes, Isanti; Kenneth B. Stokes, Brooklyn Park; Peter J. Pohndorf, Stillwater; Keith J. Proctor, Lino Lakes, all of Minn.

[73] Assignee: Medtronic, Inc., Minneapolis, Minn.

[21] Appl. No.: 189,825

[22] Filed: Feb. 1, 1994

[51] Int. Cl.⁶ ..................................................... A61N 1/05
[52] U.S. Cl. ......................... 607/120; 607/132; 607/129
[58] Field of Search ................................. 607/120, 116, 607/119, 122, 126, 128, 129, 132

[56] References Cited

U.S. PATENT DOCUMENTS

| | | | |
|---|---|---|---|
| H356 | 11/1987 | Stokes et al. | 128/785 |
| Re. 28,990 | 10/1976 | Hon et al. | 128/2.06 E |
| 3,244,174 | 4/1966 | Wesbey et al. | 128/418 |
| 3,333,045 | 7/1967 | Fisher et al. | 174/20 |
| 3,474,791 | 11/1969 | Bentov | 128/418 |
| 3,880,169 | 4/1975 | Starr et al. | 128/418 |
| 4,010,758 | 3/1977 | Rockland et al. | 128/418 |
| 4,149,542 | 4/1979 | Thorén | 128/418 |
| 4,341,226 | 7/1982 | Peters | 128/784 |
| 4,506,680 | 3/1985 | Stokes | 128/786 |
| 4,577,642 | 3/1986 | Stokes | 128/784 |
| 4,603,704 | 8/1986 | Mund et al. | 128/784 |
| 4,606,118 | 8/1986 | Cannon et al. | 29/825 |
| 4,677,989 | 7/1987 | Robblee | 128/784 |
| 4,711,251 | 12/1987 | Stokes | 128/784 |
| 4,773,433 | 9/1988 | Richter et al. | 128/784 |
| 4,784,160 | 11/1988 | Szilagyi | 128/784 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,964,414 | 11/1990 | Handa et al. | 128/784 |
| 5,085,218 | 2/1992 | Heil, Jr. et al. | 128/642 |
| 5,086,787 | 2/1992 | Grandjean et al. | 128/786 |
| 5,143,090 | 9/1992 | Dutcher et al. | 128/785 |
| 5,154,183 | 10/1992 | Kreyenhagen et al. | 128/785 |
| 5,217,027 | 6/1993 | Hermens | 128/784 |
| 5,241,957 | 9/1993 | Camps et al. | 607/119 |

*Primary Examiner*—William E. Kamm
*Assistant Examiner*—Kennedy J. Schaetzle
*Attorney, Agent, or Firm*—Michael J. Jaro; Harold R. Patton

[57] ABSTRACT

A chronic myocardial pacing lead for the delivery of stimulation energy to and the sensing of electrical signals from the myocardium of a human heart. In one embodiment the lead is bipolar, having a sleeve electrode implanted into the myocardium and a pad electrode positioned on the epicardium. The lead includes a drug for delivery through the sleeve electrode to the myocardium. The disclosed lead is highly flexible to minimize tissue reaction, this permits the lead to offer relatively low pacing thresholds, high impedance, and excellent sensing in a configuration which is relatively easy to implant.

25 Claims, 5 Drawing Sheets

STEROID ELUTING STITCH-IN CHRONIC CARDIAC LEAD

FIELD OF THE INVENTION

This invention relates to an electrical lead used to provide electrical signals to a tissue, and especially a human organ, such as a heart, and more particularly, to a chronically implanted steroid eluting cardiac lead.

BACKGROUND OF THE INVENTION

Electrical stimulation of body tissue and organs is often used as a method of treating various pathological conditions. Such stimulation generally entails making an electrical contact between body tissue and an electrical pulse generator through use of one or more stimulation leads. Various lead structures and various techniques for implanting these lead structures into body tissue and particularly the heart have been developed.

For example, a transvenous endocardial lead establishes electrical contact between an electrical pulse generator and heart through placement of a lead in the venous system. Specifically, an electrical lead is passed through a vein, with the assistance of a fluoroscope, into the heart where it is held in contact with the endocardium by the trabeculae of the heart chamber, such as the ventricle.

There are, however, disadvantages to this type of lead, including: possible damage to the vein, such as perforation or laceration during insertion; possible failure to securely attach and maintain electrical contact with the heart; possible perforation of the heart wall by the lead; and because direct visual inspection of the lead placement is not possible, possible improper lead placement in the heart.

Besides these possible problems, there are additional situations in which the installation of a transvenous endocardial pacing lead is either not feasible or not recommended. These situations include the case when the vein which would be used is damaged or too small, or the situation in which a physical or anatomical anomaly prevents the placement of a transvenous endocardial lead within the heart, such as the presence of an artificial heart valve.

In particular a transvenous endocardial lead is often either not feasible or recommended in children. One problem presented by use of a transvenous endocardial lead stems from the growth a child undergoes. Specifically, upon chronic implantation of a transvenous lead the lead body is subject to fibrotic encapsulation within the venous system. This encapsulation fixes the lead body in place, especially relative to the walls of the venous system. Over time, as the child grows the venous system elongates. Because the lead is fixed by fibrotic growth, as the venous system elongates the lead electrode will be pulled or dislodged from effective contact with the endocardium. In addition, because the venous system of a child is smaller than an adult, it is less tolerant of the partial occluding of a vein by a transvenous lead. In these cases use of an myocardial lead applied from the epicardium is often indicated or preferred.

A myocardial lead offers a significant advantage to a transvenous endocardial lead with regards to children. Because a myocardial lead is attached to the heart not through the venous system but rather through a thoracic access, a sufficient amount of spare lead length to accommodate growth may be located or looped within the thoracic cavity. In addition a myocardial lead does not even partially occlude a part of the relatively small venous system of a child.

A number of different myocardial leads have been developed, as have various techniques for implanting them within the myocardial tissue of the heart. Typically, myocardial leads are attached from the exterior of the heart through a thoracic access.

One form of such lead is a screw-in lead. This lead consists of a rigid helical coil which is used to fix the electrode to the myocardial tissue. Examples of such a lead may be found in U.S. Pat. No. 5,154,183 to Kreyenhagen et al., U.S. Pat. No. 5,143,090 to Dutcher et al., U.S. Pat. No. 5,085,218 to Heil Jr. et al., and U.S. Pat. No. 4,010,758 to Rockland et al. One problem which has been found to exist with such leads, however, is the inflammatory tissue reaction (or foreign body response) of the tissue to the device and especially the rigid helix. Inflammatory tissue reaction is caused, in part, from the presence of a foreign object within the tissue. It has been found that the presence of a rigid structure within the myocardium chronically creates at least some of the immediately surrounding myocardial tissue to be replaced with either fat or collagen or both. Such tissue reaction detrimentally affects the electrical properties of the surrounding tissue, and thus the lead performance.

One means of treating the inflammatory response has been to provide a means for delivering a drug near the electrode to mitigate the inflammatory tissue reaction described above. Specifically it has been found eluting an anti-inflammatory agent, such as a glucocortico steroid, minimizes tissue irritation, helps reduce or eliminate threshold peaking and further assists in maintaining low acute and chronic pacing thresholds.

In addition a tissue reaction due to the mechanical motion of the cardiac tissue relative to the helical coil has been found to arise in the surrounding tissue. Because the heart is a constantly moving organ, the presence of a stationary and stiff fixation coil exacerbates the normal build-up of collagen and fat near the helical coil. Such tissues may detrimentally affect the electrical performance of the surrounding tissue. As a result stimulation thresholds may rise. As such, a chronic lead which mitigates such tissue reactions would be of benefit.

Maintenance of stimulation thresholds is an important criterion for a chronically implanted cardiac lead. Implantable pulse generators are powered by a battery having a limited life. After an extended period of time, such as five years, the battery will be depleted and the implanted pulse generator must be surgically replaced. Therefore, it is an objective to minimize the electrical current drain on the power source by appropriate design of the pacemaker's electrodes and to provide for reduced stimulation voltage.

SUMMARY OF THE INVENTION

It is an object of the invention to provide a bipolar myocardial lead which permits bipolar pacing or sensing with the installation of only a single lead to a patient's heart or to another organ of the patient, which lead is simple to implant and provides a highly secure fixation.

It is another object of this invention to provide a myocardial lead which provides highly secure fixation while minimizing tissue inflammation.

It is another object of this invention to provide a myocardial lead which minimizes the electrical current drain on the power source by appropriate design of the electrode and to provide for reduced stimulation voltage.

It is another object of this invention to provide a myocardial lead which permits the elution of an anti-inflammatory agent at the electrode-tissue interface to assist in maintaining low acute and chronic pacing thresholds.

In accordance with the above objects there is provided a bipolar myocardial lead having two electrodes. The first electrode is designed to be implanted within the myocardium while the second electrode is designed to be positioned on the epicardial surface of the heart. Fixation of the lead is accomplished through a length of coiled suture attached at one end of the lead. The electrodes are configured for directional electrical stimulation. The lead includes a drug for delivery through an electrode to the myocardium. Such a lead offers relatively low pacing thresholds, efficient high pacing impedance, and excellent sensing in a configuration which is relatively easy to implant.

BRIEF DESCRIPTION OF THE DRAWINGS

These and other objects and advantages of the present invention may be fully understood and appreciated in conjunction with the attached drawings and the following detailed description of the preferred embodiments where the same numerals are employed to denote the same or similar features throughout. The drawings are not necessarily to scale.

DETAILED DESCRIPTION OF THE INVENTION

Figure 1:
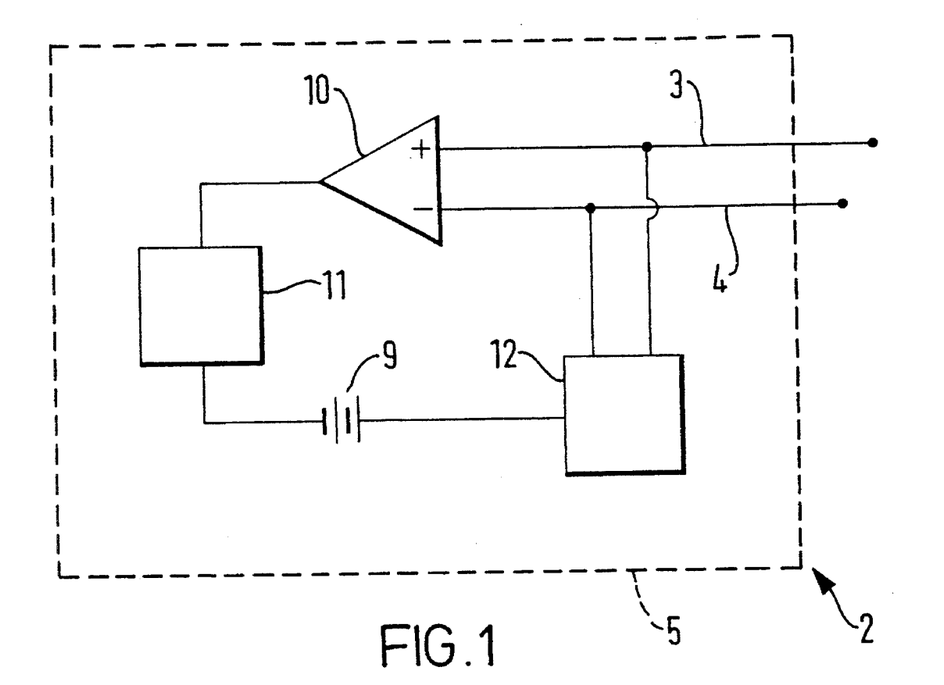
FIG. 1 is a schematic view of a lead in use with an implantable pulse generator system.

FIG. 1 is a schematic view of a lead in use with a pacing system 2, showing conductors 3, 4 electrically connected to an implantable pulse generator 5. Implantable pulse generator 5 is constructed from a battery 9, a sense amp 10, a microprocessor 11, and an output amp 12. Through such a pacing system 2 the lead of the present invention may be used to electrically stimulate and sense body tissue, such as a heart.

Figure 2:
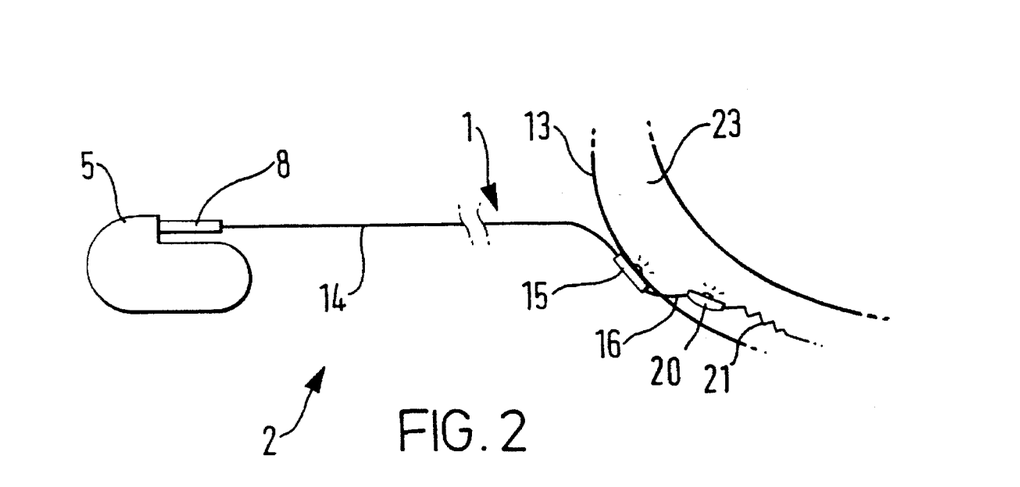
FIG. 2 is a lead according to the present invention attached to a heart and an implantable pulse generator system.

FIG. 2 shows a lead 1 according to the present invention in use as part of a pacing system 2 and implanted within a heart 13. Lead 1, as seen, has essentially seven parts or sections: connector 8, lead body 14, pad electrode 15, secondary-lead body 16, sleeve electrode 20, suture 21 and needle 22 (not shown in FIG. 2 but shown in FIG. 4.) As seen pad electrode 15 is positioned on the surface of heart 13 and sleeve electrode 20 is implanted within the cardiac tissue, and specifically within myocardium 23.

As seen in FIG. 2 connector pin 8 electrically connects implantable pulse generator 5 to lead 1, and specifically to lead body 14. A cross-section of lead body 14 may be seen in FIG. 3. As seen lead body 14 is constructed from a multi-lumen insulative cover 24 and conductors 25. Insulative cover 24 is constructed from a composite of materials, in the preferred embodiment outer tube 34 is polyurethane and inner tube 35 is polyvinylidene fluoride. Inner tube 35 provides longitudinal stiffness to lead body 14 to prevent it from stretching during implantation and possible repositioning, as described below. Although polyvinylidene fluoride is the preferred material for inner tube 35, other materials which provide a lead body having sufficient longitudinal stiffness may also be used. Insulative cover 24 has four lumens 30, 31, 32 and 33, three of which 30–32 each have a conductor, and the fourth 33 having three conductors. In the preferred embodiment the three central conductors 25 are electrically connected to pad electrode 15 while the other conductors are electrically connected to the sleeve electrode 20.

Figure 3:
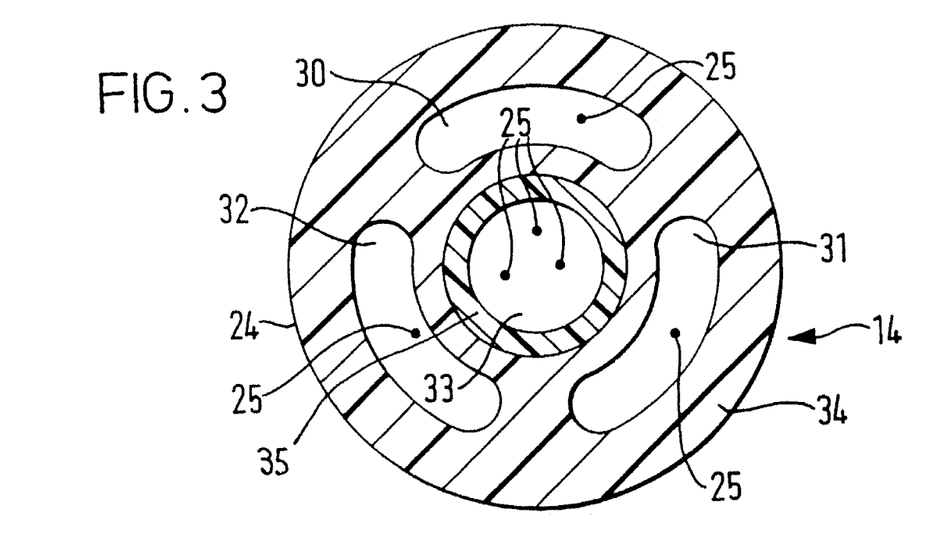
FIG. 3 is a cross-sectional view of the lead body of a lead according to the present invention.

In the preferred embodiment conductors 25 are a bundled stranded wire. A suitable bundled stranded wire may be formed from a bundle of nine wires, each made from a MP35N alloy and having a diameter of 0.001 inches, the bundle then drawn through a die to yield a bundle diameter of 0.005 inches. Although in the preferred embodiment conductors 25 are bundled stranded wire, other conductor embodiment may be used, such as, for example, multifilar wire and coiled conductors. Further details concerning the design and construction of a multi-lumen lead body and BSW conductors may be found in the U.S. patent application Ser. No. 07/994,755 of Pohndorf et al. entitled "Crush Resistant Lead Body Using BSW Conductors" filed Dec. 22, 1992 and the U.S. patent application Ser. No. 07/994,756 of Molacek et al. entitled "Medical Electrical Lead" also filed Dec. 22, 1992, now U.S. Pat. No. 5,303,704, each which is incorporated herein by reference.

Figure 4:
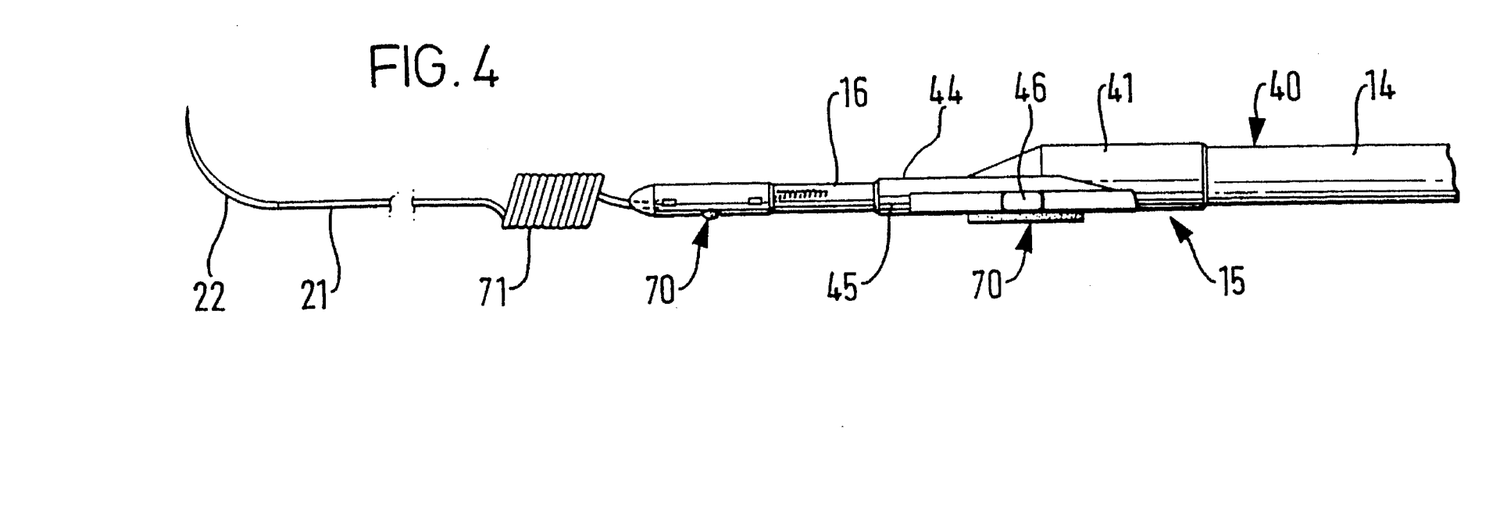
FIG. 4 is a plan view of the distal end of a lead according to the present invention.
Figure 5:
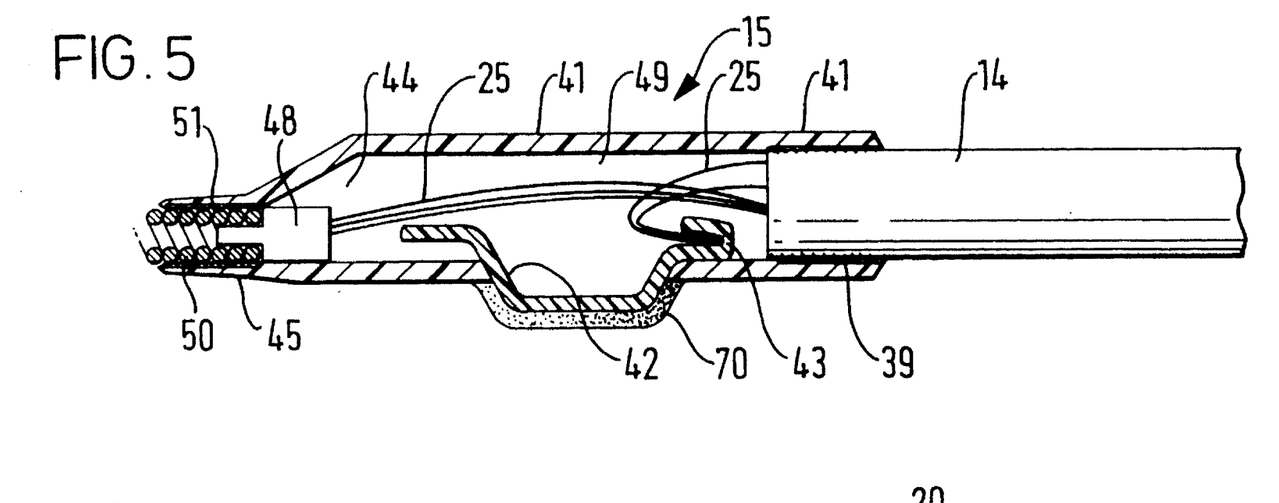
FIG. 5 is a cross-sectional view of the pad electrode used in a lead according to the present invention.
Figure 12:
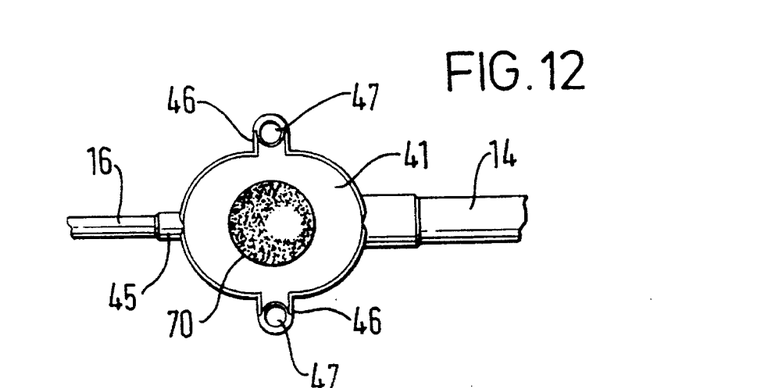
FIG. 12 is a plan view of a pad electrode used in a lead according to the present invention.

FIG. 4 is a plan view of distal end 40 of lead body 14 showing pad electrode 15 connected thereto. Pad electrode 15 is constructed from pad housing 41 and pan 42, as best seen in FIG. 5. Pad housing 41 has a pair of fixation wings 46, as seen in FIGS. 4 and 12. Holes 47 in fixation wings 46 permit pad electrode 15 to be fixed by sutures to heart. Other methods of fixing pad electrode 15 to heart may be used besides sutures, including, for example, fibrin glue, cyanoacrylate adhesive, staples, or the provision of a polyethylene terephthalate mesh on the lower surface of pad housing 41. As seen in FIG. 5, region 49 within pad housing 41 is back filled with silicone medical adhesive during assembly to fix pan 42 in place. Pan 42 features a crimp-cover 43 to crimp about conductors 25 and thereby electrically connect conductors 25 of lead body 14. Pan 42 is covered by electrode material 70. Distal end 44 of pad housing 41 features a skirt-portion 45 into which secondary-lead body 16 is attached.

Figure 6:
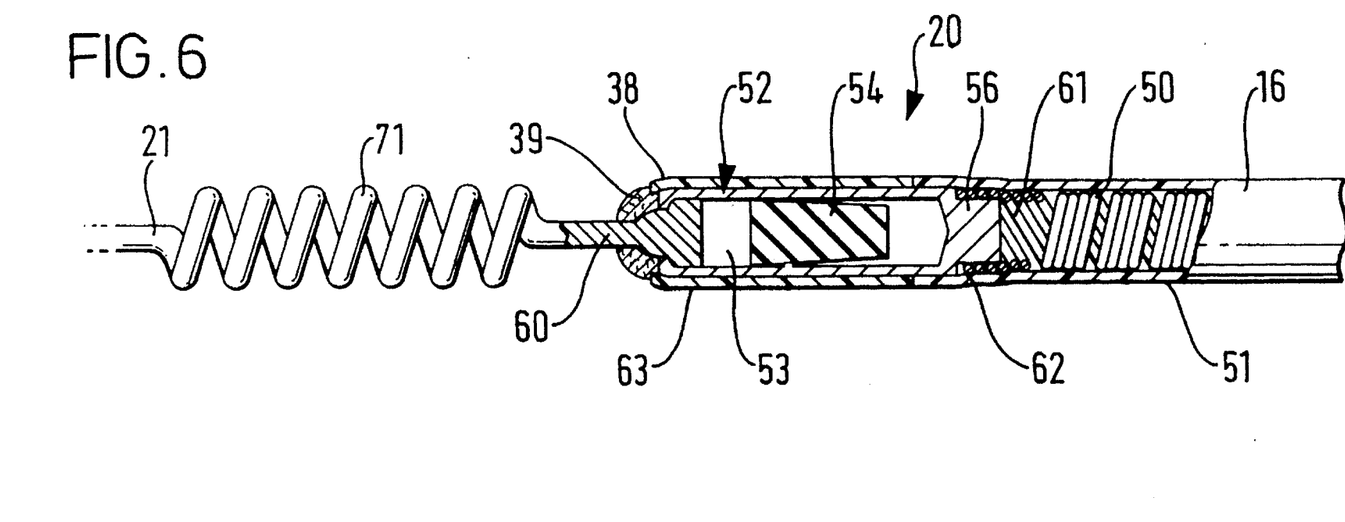
FIG. 6 is a cross-sectional view of the sleeve electrode used in a lead according to the present invention.

Secondary-lead body 16, as best seen in FIGS. 5 and 6 consists of a secondary-conductor 50 surrounded by an secondary-insulative cover 51. Secondary-insulative cover 51 is made from a biocompatible insulative material, preferably polyurethane although silicone rubber may also be used. Secondary-conductor 50 is a coiled conductor. A coiled conductor is preferred because this portion of the lead 1 rides directly upon, and within, heart 13 and thus is subject to compressive loading during cardiac contraction. Of course it should be understood that other conductors besides a coiled conductor may be provided for secondary-conductor 50 without departing from the scope of the present invention. Secondary-conductor 50 is connected to conductors 25 by junction 48. Specifically junction 48 is crimped about conductors 25. Junction 48 is further welded to secondary-conductor 50. Secondary-conductor 50 is preferably constructed from a MP35N alloy although a platinum iridium alloy may also be used.

FIG. 6 is a cross-sectional detail view of the directional sleeve electrode 20. FIG. 7, 8, 9, 10 and 11 show further details of sleeve electrode 20 and particularly formed tube 52 used in lead 1 according to the present invention. As seen sleeve electrode 20 is constructed from a formed-tube 52 having a central-cavity 53. As seen in FIG. 6, sleeve electrode 20 has a distal end having a slight taper 38. The use of taper 38 along with the thin cylindrical shape of formed tube 52 permits sleeve electrode 20 to be readily inserted into the heart with a minimum of irritation and damage to the tissue. The precise angle of taper 38 may vary and still be within the scope and spirit of the present invention. In addition a small amount of a medical adhesive 39 or any other biocompatible material may be provided at distal end of sleeve electrode 20 in order to further increase the streamline shape of sleeve electrode 20. As discussed above minimizing the trauma of lead insertion, as well as minimizing the trauma caused by the chronic implantation of a rigid electrode, is important to thereby minimize tissue reaction and thus thresholds.

Figures 7, 8:
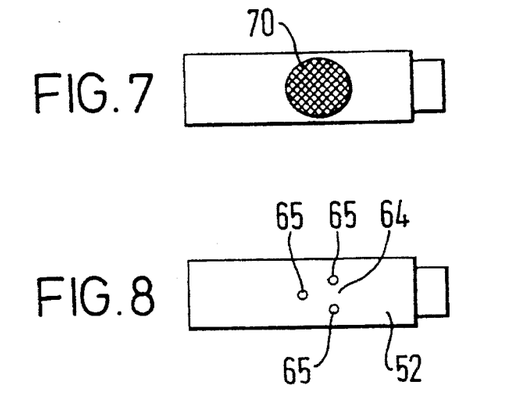
FIG. 7 is a plan view of a sleeve electrode used in a lead according to the present invention.
FIG. 8 is a plan view of a formed tube used in the sleeve electrode of the present invention.
Figure 9:
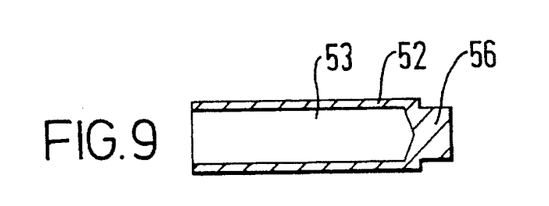
FIG. 9, 10 and 11 are cross-sectional views of the formed tube used in the sleeve electrode of the present invention.
Figure 10:
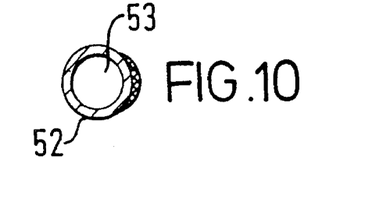
Figure 11:
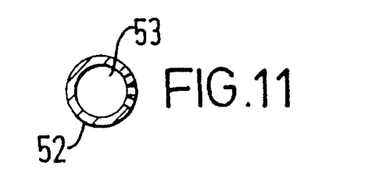

As previously mentioned, sleeve electrode 20 further has located within central-cavity 53, in the preferred embodiment, a monolithic controlled release device (MCRD) 54. MCRD 54 is preferably constructed from silicone rubber and a glucocortico steroid. Formed-tube 52 is constructed from a biocompatible conductive material, in the preferred embodiment a platinum-iridium alloy. Distal end of formed-tube 52 is crimped about proximal end 60 of suture 21. As seen, proximal end 60 of suture 21 is deformed to increase its diameter and thereby permitting crimping to accomplish a joint. Proximal end 56 of formed tube 52 is attached to distal end 61 of secondary-conductor 50, preferably by a series of welds 62. Substantially all of formed tube 52 is covered by an insulative material 63, such as by medical adhesive or polyurethane or any other suitable biocompatible insulative material, except for area 64 proximate holes 65. Area 64 is covered by porous electrode material 70, as best seen in FIG. 7. Holes 65 in formed-tube 52 allow MCRD 54 to communicate to tissue proximate sleeve electrode 20. Communication between central cavity 53 and the tissue proximate sleeve electrode 20 is important because it permits use of asteroid or other drug with the electrode. Specifically sleeve electrode 20 may be configured to allow the drug to be eluted through or around the electrode material 70 in order to reduce the acute and chronic inflammation occasioned by the foreign body response to the lead and in particular in the region proximate electrode material 70.

The anti-inflammatory agent, preferably a derivative of dexamethasone, such as the steroid dexamethasone sodium phosphate, is loaded in MCRD 54. The steroid also is deposited within the pores of porous electrode material 70 by application of a solution of dexamethasone sodium phosphate dissolved in a mixture of isopropanol and distilled or deionized water. The small geometric electrode size of sleeve electrode 20 is intended to produce very high pacing impedance. The porous surface of electrode material 70 together with platinum black electroplating contribute to a microscopically large surface area for low polarization and relatively low source impedance. The porosity of electrode material 70 also facilitates the elution of steroid, adhesion of the platinum black to the electrode surface as well as the chronic fixation of the electrode 20 to the myocardial tissue.

Electrode material 70 is preferably a porous platinum composition coated with platinum black. The porosity, together with the platinum black coating is intended to reduce source impedance and polarization. Although platinum is the preferred material for electrode material 70, it may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others and may not be effectively used together. The limitations of specific materials for use with others is well known in the art. Examples of acceptable electrode materials and associated fabrication techniques employed to achieve the micro-porous structure may be found in Stokes, U.S. Pat. No. 4,506,680 and related Medtronic U.S. Pat. Nos. 4,577,642; 4,606,118 and 4,711, 251 and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603, 704; Skalsky et al., U.S. Pat. No. 4,784,161; Szilagyi, U.S. Pat. No. 4,784,160, each of which is herein incorporated by reference.

As seen sleeve electrode 20 features an electrode surface in only one direction, i.e. only in the direction of area 64. A directional electrode has been found beneficial because it limits the electrical field to be propagated from the electrode to the specific tissue of interest, e.g. the myocardium, while concurrently minimizing the exposure of other tissues, e.g. diaphragm or nerves, to the same electrical field. In addition, because the electrical field is more precisely emitted, the active area of the sleeve electrode 20 may be decreased to thereby achieve a higher pacing impedance. In addition, this design further permits the sleeve electrode 20 to be positioned at a point where the electrode is proximal to desired sections of the myocardium as well as permitting placement within the epicardium at the optimal sensing vector. Design of sleeve electrode 20, moreover, besides permitting directional stimulation and sensing also permits the incorporation of an MCRD as well as presenting an easy to insert profile. In the preferred embodiment sleeve electrode 20 electrically communicates with the myocardial tissue in a direction perpendicular to the longitudinal axis of the lead, as best seen in FIG. 4. Other directions may, however, be used, such as an electrode which would electrically communicate with the myocardial tissue in a direction parallel to the longitudinal axis of the lead. In fact any specific direction may be used.

Pad electrode 15 has a surface area approximately ten times (10×) greater than sleeve electrode 20. In the preferred embodiment pad electrode 15 has a surface area of 12 mm sq. and sleeve electrode 20 has a surface area of 0.8 mm sq.

Figure 13:
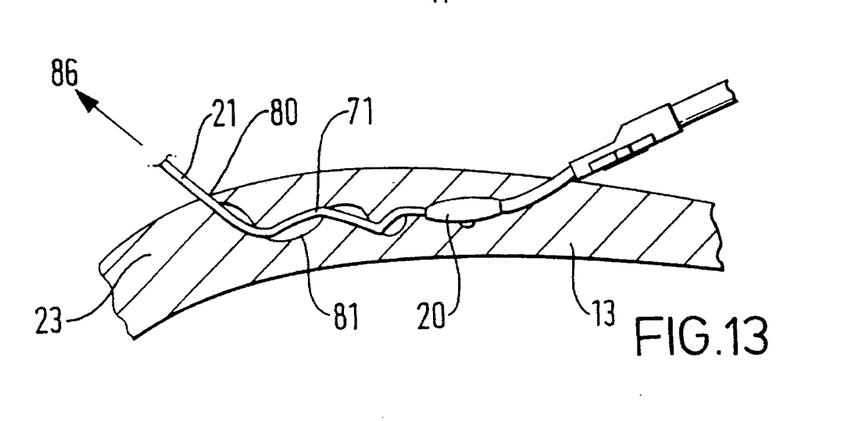
FIG. 13 is shows the lead as it is being positioned within the myocardium.

Implantation of lead 1 is begun by inserting atraumatic needle 22 through myocardial tissue 23 to it exits at location 80. As seen in FIG. 13, suture 21 is pulled until sleeve electrode 20 is properly positioned within part of channel 81, in electrical contact with tissue of heart 13. Suture 21 is preferably PROLENE. Tension is exerted on coiled section 71 by pulling suture 21 in direction of arrow 86, and the resistive friction between sleeve electrode 20 and heart 13 causes coiled section 71 to stretch and become temporarily elongated.

While tension is continuously applied to suture 21 for maintaining coiled section 71 in its extended and elongated state, suture 21 is severed with a conventional cutting instrument, such as a pair of scissors to remove excess portion and dispose of needle 22.

Figure 14:
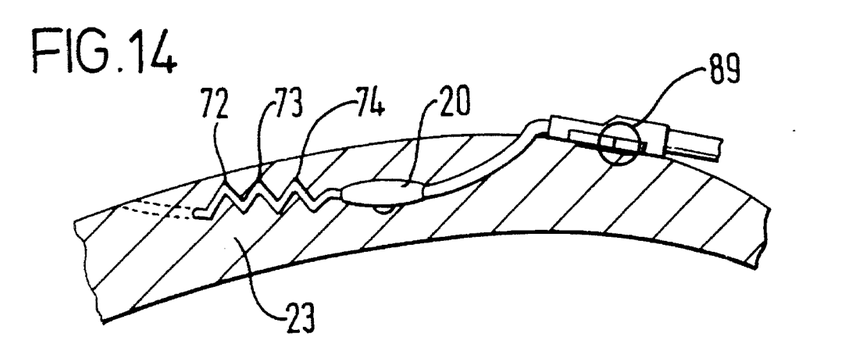
FIG. 14 shows the lead chronically implanted after the suture has been cut and the pad electrode sutured in place.
Figure 15:
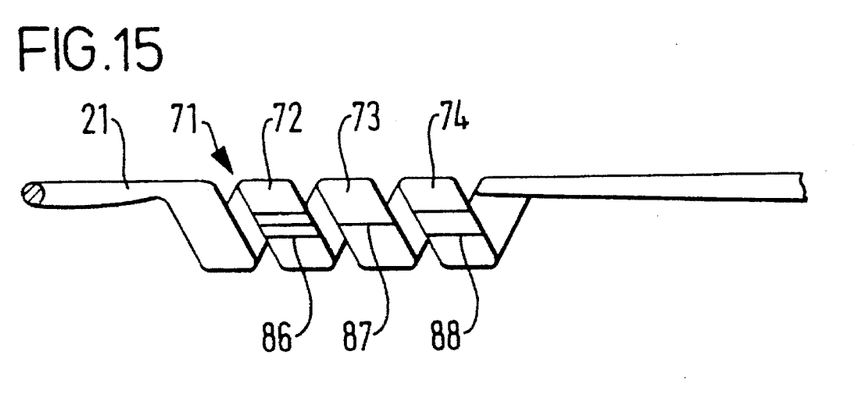
FIG. 15 shows a detail of coiled section of suture having identification markings.

In some applications it may be desirable to sever suture 21 at a point which includes at least a part of the coils 71. This will ensure only a selected number of turns 72, 73 and 74, as seen in FIG. 14, are left inside channel 81. The number of turns may be selected by the surgeon, depending on whether lead 1 is inserted in the atrial or ventricular wall, and depending on the age or physical condition of the patient. If lead 1 is used for ventricular applications,for example, it may be acceptable to leave most, if not all of turns 72, 73 and 74 within channel 81 of the myocardium tissue 23. If lead 1 is used for pediatric or atrial applications, however, then a lesser number of turns 72 and 73 of coiled section 71 might be used to retain lead 1 in place. In order to facilitate the selection process the lead 1 of the present invention may feature coding along suture 21 as disclosed in U.S. Pat. No. 5,217,027 to Hermens and incorporated herein by reference. Special coding along suture 21 may be accomplished through a series of color codings or identification marks along suture 21 to indicate to the surgeon the length to which the suture 21 must be pulled through myocardium tissue 23 in order to retain lead in position. In the present illustration shown in FIG. 15, markings 86, 87 and 88, such as a color coded indentation, visually indicate to the surgeon the number of turns 72, 73 and 74 within channel 81.

Once electrode is satisfactory positioned suture 21 is cut to the desired length and coiled section 71 retracts towards sleeve electrode 20 within channel 81. Coiled section 71, due to the compressive elasticity of turns 72, 73 and 74, wedges in the myocardial tissue 23 and thereby firmly affixes sleeve electrode 20 in tissue 23. If lead 1 is unsatisfactorily positioned, however, it may be removed by gently retracting it from channel 81 through traction along lead body 14. Lead 1 may then be reinserted at the next desired site as described above, assuming, of course that suture 21 and in particular needle 20 has not been separated.

Once sleeve electrode 20 is positioned, pad electrode 15 is placed flush against the surface of myocardial tissue 23. If desired pad electrode 15 may be sutured in place through the use of suture holes 27 and suture 89, although suturing is not always necessary.

Figure 16:
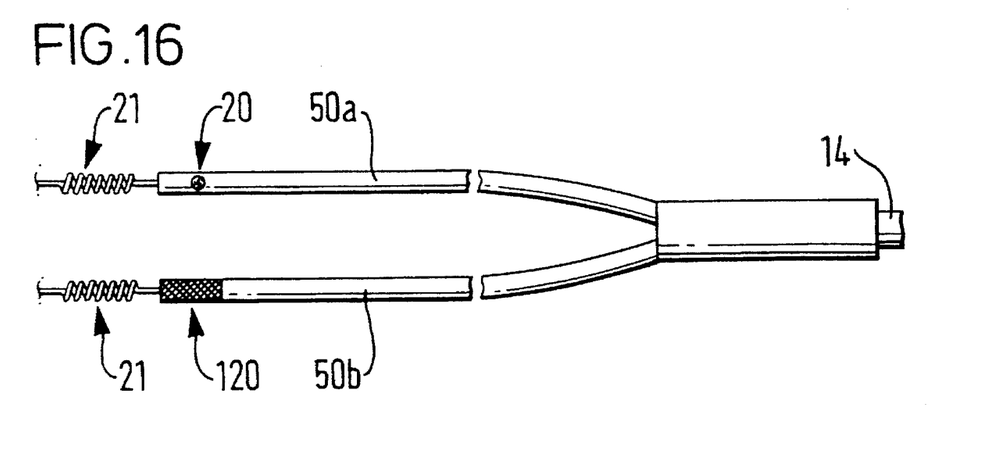
FIG. 16 depicts a plan view of the distal end of an alternate embodiment of a lead according to the present invention.

FIG. 16 depicts a plan view of the distal end of an alternate embodiment of a lead according to the present invention. As seen this embodiment is similar to that previously described with the exception of having a pair of secondary-conductors 50a and 50b, each having an electrode. As seen the sleeve electrode 20 on secondary-conductor 50a is similar to that previously described. Electrode 120 on secondary-conductor 50b is constructed in a similar manner as sleeve electrode 20 with the exception of not being directional nor utilizing an MCRD 53. In addition electrode 120 has a surface area approximately ten times (10×) greater than sleeve electrode 20, in the preferred embodiment electrode 120 has a surface area of 12 mm sq. and sleeve electrode 20 has a surface area of 0.8 mm sq.

Installation of this embodiment is the same as described above, but requiring a pair of sutures 21 to be inserted. Although not shown, each suture has a needle 20 attached to it.

The present invention may further be incorporated within a unipolar lead. Such a unipolar embodiment would differ from the bipolar embodiment through the absence of either pad electrode 15 or sleeve electrode 20.

While the embodiment of the present invention has been described in particular applications, it will be understood the invention may be practiced in other lead and electrode technologies where the aforementioned characteristics are desirable, including neurological and muscle stimulation applications.

Furthermore, although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A lead for establishing electrical contact between body tissue and a medical device, said lead having a longitudinal axis, said lead comprising:

a length of flexible conductor having a distal end and a longitudinal axis, said conductor having an insulative casing;

a member electrically connected to said conductor, said member having an insulative covering, said member being cylindrical and coaxial with said longitudinal axis of said flexible conductor, said member having a chamber, said chamber communicating with an exterior of said insulative covering in a first direction through a port, said port being perpendicular to said longitudinal axis of said lead, a porous conductive material electrically connecting said member to said exterior of said insulative covering in a direction perpendicular to said longitudinal axis of said flexible conductor, said porous conductive material having a first surface area, said member having means for dispensing a drug positioned in said chamber;

a length of suture having a coiled portion connected to said member; and a needle attached to an end of said suture.

2. A lead according to claim 1 further comprising a second member electrically connected to said conductor, said second member having an insulated area and an exposed area, said exposed area having a second surface area of at least ten times greater than said surface area of said porous conductive material.

3. A lead according to claim 2 wherein said length of suture is attached to an end of said second member.

4. A lead according to claim 2 wherein said surface area of said porous conductive material is 0.8 mm sq. and said second surface area of said second member is 12 mm sq.

5. A leading according to claim 2 wherein said exposed area of said second member is perpendicular to said longitudinal axis of said lead.

6. A lead according to claim 2 wherein said exposed area of said second member is cylindrical.

7. A lead for establishing electrical contact between body tissue and a medical device, said lead having a longitudinal axis, said lead comprising:

a length of flexible conductor having a distal end and a longitudinal axis, said conductor having an insulative casing;

a member electrically connected to said conductor, said member having an insulative covering, said member being cylindrical and coaxial with said longitudinal axis of said flexible conductor, said member electrically communicating with an exterior of said insulative covering in a first direction to said longitudinal axis of said lead;

a length of suture having a coiled portion coupled to said member; and a needle attached to an end of said suture.

8. A lead according to claim 7 wherein said member has a chamber, said chamber communicating with said exterior of said insulative covering through a port, means for dispensing a drug positioned in said chamber.

9. A lead according to claim 7 wherein said member has a porous conductive material, said member electrically communicating with said exterior of said insulative covering in a first direction perpendicular to said longitudinal axis of said lead through said porous conductive material.

10. A lead according to claim 9 wherein said porous conductive material has a first surface area.

11. A lead according to claim 8 further comprising a porous conductive material positioned over said port to thereby permit said chamber to communicate with said exterior of said insulative covering through said port and to permit said member to electrically communicate with an exterior of said insulative covering in a first direction perpendicular to said longitudinal axis of said lead.

12. A lead according to claim 7 further comprising a second member electrically connected to said conductor, said second member having an insulated area and an exposed area, said exposed area having a surface area of at least ten times greater than a first surface area of a porous conductive material mounted to said first member.

13. A lead according to claim 8 wherein said length of suture is attached to an end of a second member electrically connected to said conductor.

14. A lead according to claim 7 wherein said first direction is perpendicular to said longitudinal axis of said lead.

15. A lead according to claim 7 wherein said first direction is parallel to said longitudinal axis of said lead.

16. A lead for establishing electrical contact between body tissue and a medical device, said lead having a longitudinal axis, said lead comprising:

a length of flexible conductor having a distal end and a longitudinal axis, said conductor having an insulative casing;

a member electrically connected to said conductor, said member having an insulative covering, said member being cylindrical and coaxial with said longitudinal axis of said flexible conductor, said member having a chamber, said chamber communicating with an exterior of said insulative covering in a first direction through a port, a porous conductive material electrically connecting said member to said exterior of said insulative covering, said porous conductive material having a first surface area, said member having means for dispensing a drug positioned in said chamber;

a length of suture having a coiled portion coupled to said member; and a needle attached to an end of said suture.

17. A lead according to claim 16 further comprising said port being perpendicular to said longitudinal axis of said lead.

18. A lead according to claim 16 wherein said first direction is perpendicular to said longitudinal axis of said lead.

19. A lead according to claim 16 wherein said first direction is parallel to said longitudinal axis of said lead.

20. A lead according to claim 16 further comprising a second member electrically connected to said conductor, said second member having an insulated area and an exposed area, said exposed area being planar and having a second surface area of at least ten times greater than said surface area of said porous conductive material.

21. A lead for establishing electrical contact between body tissue and a medical device, said lead having a longitudinal axis, said lead comprising:

a length of flexible conductor having a distal end;

a first member connected to said distal end of said flexible conductor, said first member having a proximal end and a distal end, said proximal end of said first member attached to said distal end of said flexible conductor, said first member having a first electrode configured to be affixed to the surface of said body tissue in a first direction perpendicular to said longitudinal axis;

a coiled conductor connected to said distal end of said first member;

a second member connected to a distal end of said coiled conductor, said second member covered by an insulative covering, said second member having a chamber, said chamber communicating with an exterior of said insulative covering by a port, a porous conductive material electrically connecting said second member to said exterior of said insulative covering in a second direction perpendicular to said longitudinal axis, said second member having means for dispensing a drug positioned in said chamber;

a length of suture having a coiled portion coupled to said second member; and a needle attached to an end of said suture.

22. A lead according to claim 21 wherein said first direction perpendicular to said longitudinal axis and said second direction perpendicular to said longitudinal axis are the same.

23. A lead according to claim 21 wherein said second member has a tapered distal end.

24. A lead according to claim 21 wherein said drug dispensing means comprises a water permeable polymer.

25. A lead according to claim 21 wherein said first electrode is formed of a conductive material selected from the class of materials essentially of platinum, palladium, titanium, tantulum, rhodium, iridium, carbon, vitreous carbon and alloys, oxides and nitrides of such metals or other conductive materials.

* * * * *